(12) United States Patent
Snyder et al.

(10) Patent No.: US 10,335,120 B2
(45) Date of Patent: Jul. 2, 2019

(54) SYSTEM AND METHOD FOR 3D ULTRASOUND VOLUME MEASUREMENTS

(71) Applicant: KONINKLIJKE PHILIPS N.V., Eindhoven (NL)

(72) Inventors: Richard Allen Snyder, Chester, NH (US); Vinodkumar Elangovan, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 533 days.

(21) Appl. No.: 14/406,760

(22) PCT Filed: Jun. 17, 2013

(86) PCT No.: PCT/IB2013/054962
§ 371 (c)(1),
(2) Date: Dec. 10, 2014

(87) PCT Pub. No.: WO2014/001954
PCT Pub. Date: Jan. 3, 2014

(65) Prior Publication Data
US 2015/0157297 A1 Jun. 11, 2015

Related U.S. Application Data

(60) Provisional application No. 61/663,652, filed on Jun. 25, 2012.

(51) Int. Cl.
*A61B 8/08* (2006.01)
*A61B 8/00* (2006.01)
(Continued)

(52) U.S. Cl.
CPC .......... *A61B 8/5223* (2013.01); *A61B 5/7405* (2013.01); *A61B 5/7455* (2013.01);
(Continued)

(58) Field of Classification Search
CPC ....... A61B 8/466; A61B 8/469; A61B 8/5223; A61B 8/483; A61B 8/54; A61B 5/7405;
(Continued)

(56) References Cited

U.S. PATENT DOCUMENTS 6,048,314 A 4/2000 Nikom
2002/0193687 A1* 12/2002 Vining ................. A61B 5/1076
600/425
(Continued)

FOREIGN PATENT DOCUMENTS

EP 2182352 A2 5/2010
JP 3325224 11/1999
JP 11299787 A 11/1999

OTHER PUBLICATIONS

Ultrasound, https://www.youtube.com/watch?v=7xay5MFDgaY, published on Jun. 26, 2011.*
(Continued)

*Primary Examiner* — Bo Joseph Peng

(57) ABSTRACT

The present invention relates to an ultrasound imaging system and a method for the measurement of a distance (58) between two points (54, 56) within a volume of a three-dimensional image (50). To avoid the commonly known fore-shortening effect, according to which a distance measured by the system is shorter than an actual distance (58) between the two points (54, 56), an in-depth control of a cursor (53) shown in the image (50) on the display as provided to the user. Further, an indication (72) may be given to the user that the cursor (53) collides with a structure (52) within the volume to allow the user to assess the movement of the cursor out of the plane shown on the display more conveniently. By this, occurrence of the fore-shortening effect may be avoided.

15 Claims, 8 Drawing Sheets

(51) Int. Cl.
*G01S 15/89* (2006.01)
*G01S 7/52* (2006.01)
*G06T 19/00* (2011.01)
*A61B 5/00* (2006.01)
*A61B 8/14* (2006.01)

(52) U.S. Cl.
CPC ............ *A61B 8/145* (2013.01); *A61B 8/4483* (2013.01); *A61B 8/466* (2013.01); *A61B 8/469* (2013.01); *A61B 8/483* (2013.01); *A61B 8/54* (2013.01); *G01S 7/52073* (2013.01); *G01S 15/8993* (2013.01); *G06T 19/00* (2013.01); *G06T 2219/012* (2013.01)

(58) Field of Classification Search
CPC ..... A61B 5/7455; A61B 8/145; A61B 8/4483; G01S 15/8993; G01S 7/52073; G06T 19/00; G06T 2219/012
See application file for complete search history.

(56) References Cited

U.S. PATENT DOCUMENTS

2011/0066031 A1 3/2011 Lee et al.
2011/0107270 A1* 5/2011 Wang .................. G06F 19/3437 715/850
2011/0184290 A1 7/2011 Yoo et al.

OTHER PUBLICATIONS

SketchUp, https://www.youtube.com/watch?v=h71Tlx8O8gU, Published on Jun. 20, 2007.*
Philips, CX50 Ultrasound System User Manual, Sep. 2008.*
SketchUP, SketchUp: Working through thick and thin, https://www.youtube.com/watch?v=UjUER6pn_B4, Published on Jun. 17, 2007.*
Solidworks, http://help.solidworks.com/2010/english/SolidWorks/sldworks/LegacyHelp/Sldworks/Fundamentals/Highlighting.htm?id=c8bd2be838f44a508b091f1c8f6ca7ab#Pg0&ProductType=&ProductName=, Published in 2010, while Internet Archive wayback machine also captured on Mar. 16, 2011.*
Solidworks, http://help.solidworks.com/2010/english/SolidWorks/sldworks/LegacyHelp/Sldworks/Parts/HIDD_MEASURE.htm?id=6fe9b40e28ab43f79963b22629de8615#Pg0&ProductType=&ProductName=, Published in 2010, while Internet Archive wayback machine also captured on Apr. 7, 2011.*

* cited by examiner

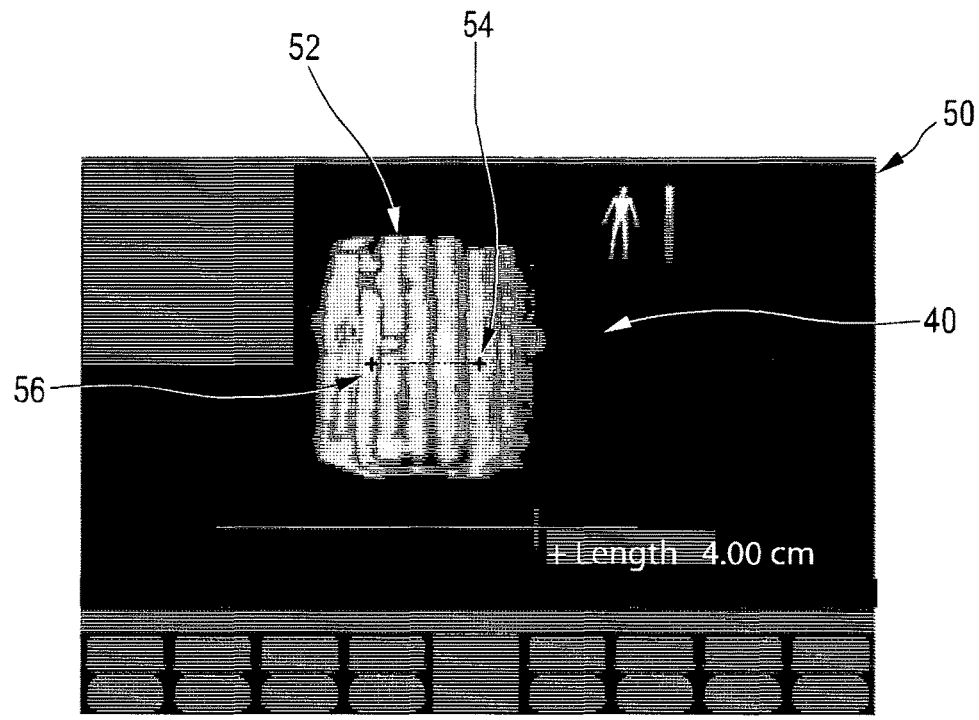
PRIOR ART FIG. 4a
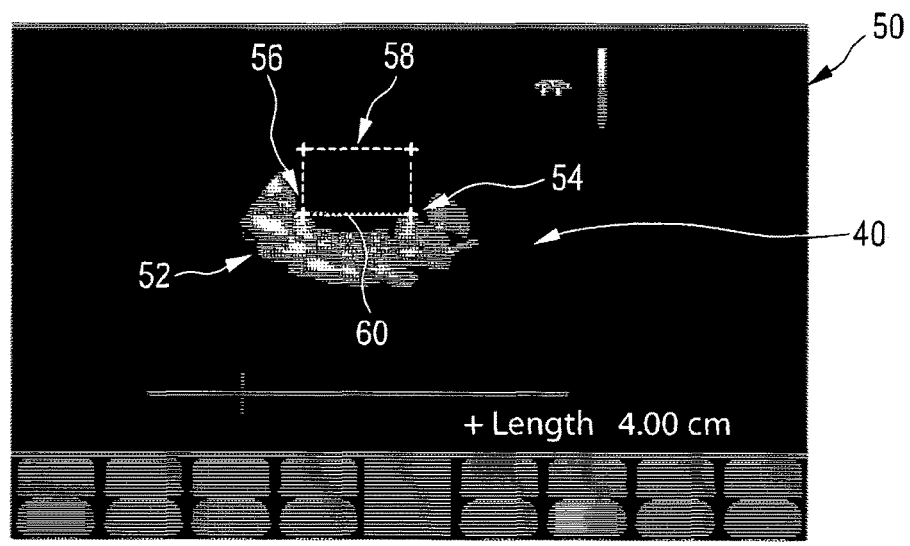
PRIOR ART FIG. 4b

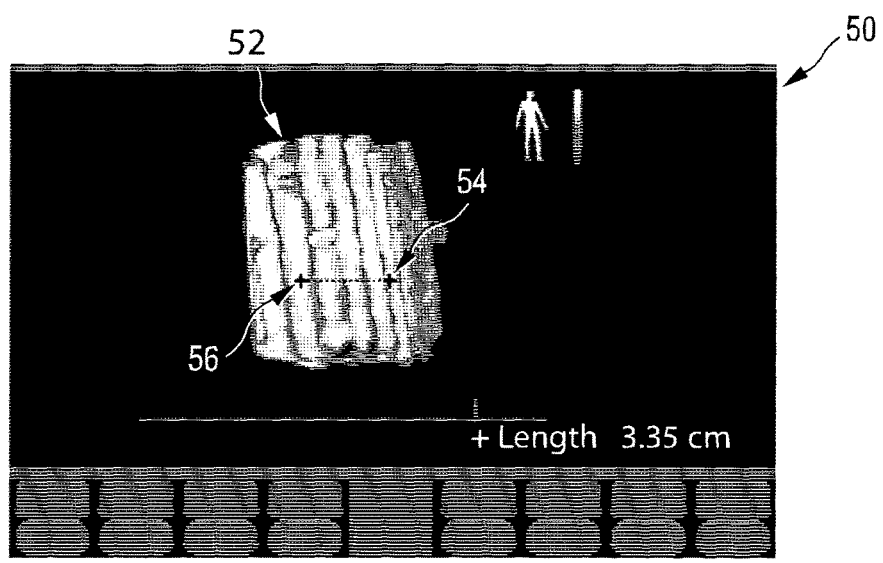
PRIOR ART FIG. 5a
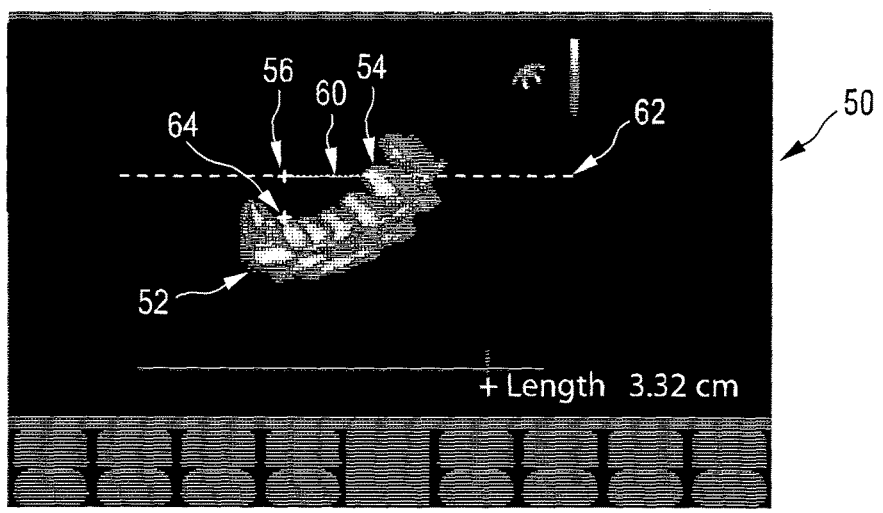
PRIOR ART FIG. 5b

SYSTEM AND METHOD FOR 3D ULTRASOUND VOLUME MEASUREMENTS

This application is the U.S. National Phase application under 35 U.S.C. § 371 of International Application No. PCT/IB2013/054962, filed on Jun. 17, 2013, which claims the benefit of U.S. Provisional Application No. 61/663,652 filed on Jun. 25, 2012. These applications are hereby incorporated by reference herein.

FIELD OF THE INVENTION

The present invention relates to an ultrasound imaging system and method for determining a distance between a first point and a second point in a three-dimensional ultrasound image of a volume, for example an anatomical site of a patient. The present invention further relates to a computer program for implementing such method.

BACKGROUND OF THE INVENTION

In three-dimensional ultrasound imaging, or volume imaging, the acquisition of a three-dimensional image is accomplished by conducting many two-dimensional scans that slice through the volume of interest. Hence, a multitude of two-dimensional images is acquired that lie next to another. By proper image processing, a three-dimensional image of the volume of interest can be built out of the multitude of two-dimensional images. The three-dimensional information acquired from the multitude of two-dimensional images is displayed in proper form on a display for the user of the ultrasound system.

Further, in three-dimensional ultrasound imaging, there is often a need to make measurements of anatomical structures within the inspected volume. For convenience to users, a measurement capability is available on three-dimensional ultrasound imaging systems where the user can conduct a measurement directly on the rendered image of the three-dimensional volume containing those anatomic structures. This so called "on-glass" measurement method is very easy and convenient for users. However this technique is susceptible to a so-called "fore-shortening effect". If the structures being measured are not in the same plane as the plane of the projected image of the three-dimensional volume, the distance measured between the structures as seen on the screen will be less than the true distance between the structures in the actual three-dimensional space.

Therefore, ultrasound systems and methods of performing measurement on three-dimensional ultrasound images have been contemplated. The reference US 2011/0066031 A1 discloses embodiments for providing an ultrasound system for performing a three-dimensional measurement and comprising an ultrasound data acquisition unit configured to transmit ultrasound signals to a target object and receive ultrasound echo signals reflected from the target object to acquire ultrasound data. Further, it comprises a user interface configured to receive input data from a user and a processor configured to form a three-dimensional ultrasound image based on volume data derived from the ultrasound data, establish two or more points on the 3D-ultrasound image based on the input data, generate connection data among the established two or more points on the 3D-ultrasound image, and measure distances among the established two or more points based on the input data and the connection data.

There is a need to further improve such three-dimensional ultrasound systems.

SUMMARY OF THE INVENTION

It is an object of the present invention to provide an improved ultrasound system and method. It is a further object of the present invention to provide a computer program for implementing such method.

In a first aspect of the present invention an ultrasound imaging system for providing a three-dimensional image of a volume is presented. The ultrasound imaging system comprises a transducer array configured to provide an ultrasound receive signal, a controlling unit configured to receive the ultrasound receive signal and to provide display data representing the three-dimensional image, wherein the controlling unit is further configured to determine a distance between a first point and a second point identified in the three-dimensional image, a display configured to receive the display data and to provide the three-dimensional image of the volume and a cursor for identifying the first point and the second point, and an input device configured to provide input data to the controlling unit, wherein the input data includes a movement of the cursor, and wherein the ultrasound imaging system is configured to enable a first movement of the cursor in a plane of the three-dimensional image provided on the display and a second movement of the cursor perpendicular to the plane.

In a further aspect of the present invention a method for determining a distance between a first point and a second point in a three-dimensional ultrasound image of a volume is presented. The method comprises the steps of displaying the three-dimensional ultrasound image on a display together with a cursor for identifying the first point and the second point, moving the cursor parallel to a plane provided on the display based on input data to identify a first coordinate and a second coordinate of at least one of the first and second points, moving the cursor perpendicularly to the plane provided on the display based on input data to identify a third coordinate of the respective point, providing an indication if the cursor collides with a structure displayed within the volume, and determining the distance between the first point and the second point.

In a further aspect of the present invention a computer program is presented comprising program code means for causing a computer to carry out the steps of such method when said computer program is carried out on the computer.

The basic idea of the invention is to overcome the "fore-shortening effect" by providing the user with the possibility to place measurement cursors directly into the volume to touch the structures that are to be measured in the three-dimensional image.

By this, the problem that the user may only place the cursor in a plane shown on the display can be overcome. Further, there is no need for the user to rotate the three-dimensional volume extensively to find a proper in which it is possible to locate the cursor at a proper position touching a structure in the three-dimensional volume. Instead, the user may position the cursor in a plane of the three-dimensional volume shown on the display first and then may "dive" the cursor into the volume until it touches the structure.

A user is provided with a cursor end-point depth control, for example for the z-dimension, in addition to the trackball for placing the end-point in the dimensions of the screen, for example the x and y dimensions. After placing the first point or the second point in the plane, e.g. with a trackball, over the structure to be measured, the user then uses the endpoint depth control to move the cursor down into the volume. After both points are placed in the same manner, the ultrasound imaging system calculates the true three-dimensional distance between the points. Then, the ultrasound imaging system may display the distance as a "length" measurement.

Due to this, it can be ensured that the first and second points are touching the structure and are not floating somewhere within the volume. Hence, the "fore-shortening effect" cannot occur.

Preferred embodiments of the invention are defined in the dependent claims. It shall be understood that the claimed method has similar and/or identical preferred embodiments as the claimed device and as defined in the dependent claims.

In one embodiment, the ultrasound imaging system is configured to enable the second movement after the first movement has been completed. By this, a user may first move a cursor within the plane shown on the display. If a proper position has been reached, the user may then fix this position and, hence, first and second coordinated of a respective first or second being determined. Subsequently, the user can move the cursor perpendicular to the plane to place the cursor properly touching the structure to be measured. By this, the third coordinate can be determined. As the first and second coordinate may remain fixed during this second movement, alignment and orientation within the three-dimensional image is facilitated.

In a further embodiment, the ultrasound imaging system is configured to enable the second movement and the first movement simultaneously. By this, the positioning of the cursor may be accelerated although an advanced navigation within the three-dimensional image is required.

In a further embodiment, the ultrasound imaging system is configured to conduct the second movement automatically. This may be the provided in case the first and second movements are conducted subsequently. However, this may also be provided in case the second movement is conducted simultaneously with the first movement. The automatic second movement may be conducted in a way that a collision detection takes pace that is able to determine a first collision between the cursor and a structure within the volume starting from the plane in which the first movement is conducted. In other words, the ultrasound imaging systems automatically moves the cursor down into the in the third dimension and detects the first point of collision between the cursor and the structure. In case the second movement is conducted subsequently to the first movement, the user may be enabled to activate the automatic second movement via the input device, for example by hitting a corresponding button. Further, the user may be enabled to manually correct the location of the point of collision. In case the first and the second movement are conducted simultaneously, the user may be enabled to leave the automatic second movement activated while conducting the first movement, i.e. altering the first and second coordinates. The corresponding third coordinate would then be determined continuously. The third coordinate may be shown to the user. By this, there may be provided the advantage that the user is able to trace a surface of the structure while conducting the first movement. This may facilitate getting an impression of the three-dimensional shape of the structure shown on the display.

In a further embodiment, the ultrasound imaging system is further configured to provide an indication if the cursor collides with a structure within the volume. By this, locating the first and second points within the volume is even further facilitated. By providing an indication, which may be of any sufficient type such as a visual indication, an audio indication or a tactually sensible indication. The user now may locate the cursor in the plane shown on the display during the first movement. Then, the second movement may be conducted without any need to change a perspective of the view shown on the display. As an indication is given in case the cursor touches or collides with a structure, for example an anatomical structure within the volume, the second movement can be conducted although it is not visible on the display since the second movement is merely perpendicular to the shown plane. This even more facilitates making inputs the ultrasound imaging system and making measurements during the observation of a volume.

In a further embodiment, the indication is a visual indication displayed on the display. By this, a user moving the cursor via the input device and watching the display can easily recognize the visual indication which may itself be displayed on the display. As a display is already in an ultrasound imaging system, no further means are necessary to provide a visual indication.

In a further embodiment, the visual indication is a change in the appearance of the cursor or a tag showing up on the display. A change of the appearance of the cursor may makes recognizing that the cursor collides with a structure more obvious. As the cursor will, of course, be observed by a user properly locating the cursor on the screen, a change in its appearance is instantly recognized. As an alternative, a tag may show up on the display. The tag may be any symbol or phrase suitable to indicate a collision between the cursor and the structure. For example, the tag may an exclamation mark or the phrase "structure touched" showing up in a part of the display. Last, the visual indication may also be a light, in particular a coloured light, lighting up when the cursor collides with the structure.

In a further embodiment, the change in the appearance of the cursor causes the cursor to light-up or to disappear. In particular, when the cursor reaches the structure, a hidden-line mechanism may cause the cursor to disappear into the structure, providing the user with a visual indication that the structure is being touched by the cursor. As an alternative, the cursor might also light-up when it is in the structure. By this, well recognizable options for a change of the appearance of the cursor are provided.

In a further embodiment, the visual indication is a change of the appearance of the structure within the volume. As the structure is usually significantly larger than the cursor, a change of the appearance of the structure may provide an even more apparent visual indication of the cursor touching the structure. A change of the appearance of the structure may be implemented, for example, as a change of the colour of the tissue and the structure, respectively. In further examples, the brightness of the structure may change additionally or alternatively to a change of the colour. Furthermore, the structure may also switch into a state of pulsation as soon as the cursor collides with the structure. Such pulsation can, for example, be implemented by a dynamic change of the colour and/or brightness of the structure.

In a further embodiment, the ultrasound imaging system further comprises a speaker, and wherein the indication is an audio indication provided via the speaker. Additionally or alternatively to the visual indication, an audio indication can be provided to the user. By this, even when not inspecting the display, the user can conduct the second movement. When the cursor touches the structure, a noise or tone provides an indication that the cursor is properly located.

In a further embodiment, the indication is tactually sensible indication provided via the input device. Additionally or alternative to each of the visual and audio indication, a tactual indication of the cursor touching the structure may be provided. For example, the input device may provide rumble movement when the cursor collides with the structure in the volume. Again, by this, even when not inspecting the display, the user can conduct the second movement. The user will receive a quick and immediate indication as soon as the cursor touches the structure.

In a further embodiment, the ultrasound system is further configured to enable inputting a measurement path between the first point and the second point, and wherein the distance is determined along the measurement path. Hence, in addition to simple point-to-point measurement, other length measurements along different measurement paths can also be accomplished.

In a further embodiment, the ultrasound system is configured to input the measurement path by identifying at least one further point within the volume and/or by selecting a geometric form to connect the first point and the second point. For example, user defined measurement paths as defined by connecting dots can be applied. Also geometrical standard forms such as ellipses, parts of circles and splines of second or even higher order can be used.

In a further embodiment, the system further comprises a beam former configured to control the transducer array to scan the volume along a multitude of scanning lines, and further configured to receive the ultrasound receive signal and to provide an image signal, a signal processor configured to receive the image signal and to provide image data, an image processor configured to receive the image data from the signal processor and to provide display data. By this, a proper signal processing and control scheme to capture and display three-dimensional images of the volume can be provided.

BRIEF DESCRIPTION OF THE DRAWINGS

These and other aspects of the invention will be apparent from and elucidated with reference to the embodiment(s) described hereinafter. In the following drawings

FIG. 4a and FIG. 4b show an in plane measurement of a distance between two points according to the prior art;

FIG. 5a and FIG. 5b show an out of plane measurement of a distance between two points and the occurrence of the "fore-shortening effect";

DETAILED DESCRIPTION OF THE INVENTION

Figure 1:
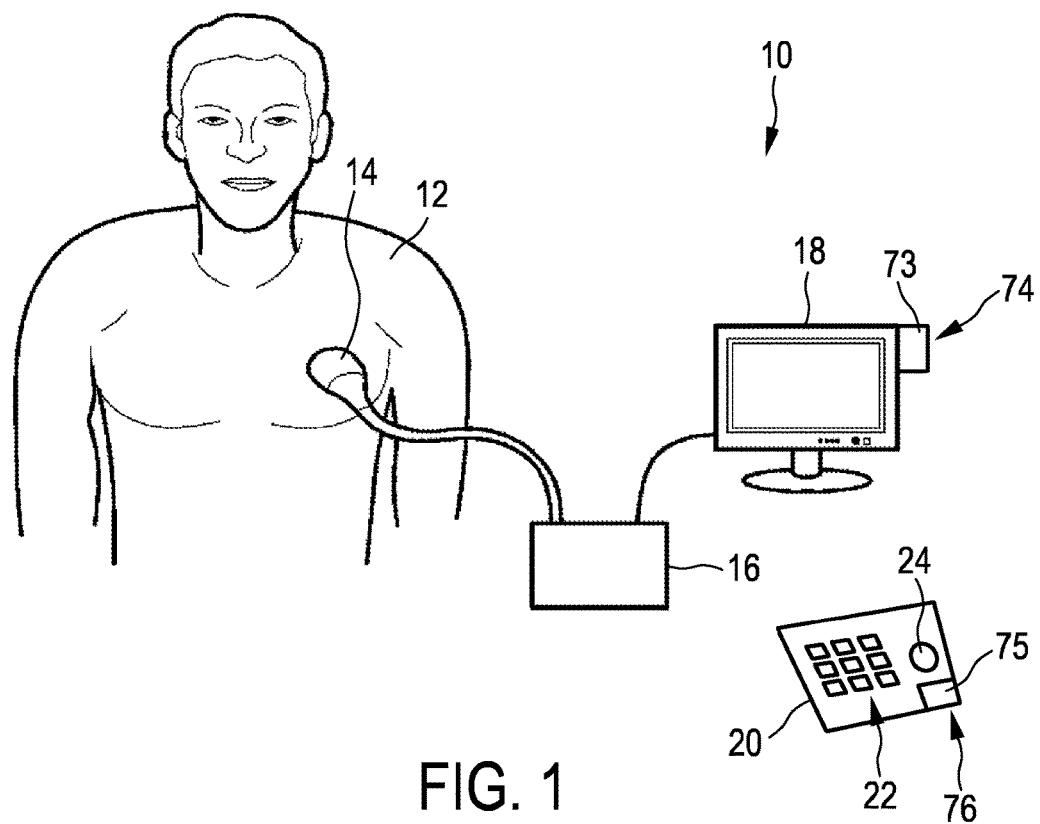
FIG. 1 shows a schematic illustration of an ultrasound imaging system according to an embodiment.

FIG. 1 shows a schematic illustration of an ultrasound system 10 according to an embodiment, in particular a medical ultrasound three-dimensional imaging system. The ultrasound system 10 is applied to inspect a volume of an anatomical site, in particular an anatomical site of a patient 12. The ultrasound system 10 comprises an ultrasound probe 14 having at least one transducer array having a multitude of transducer elements for transmitting and/or receiving ultrasound waves. In one example, the transducer elements each can transmit ultrasound waves in form of at least one transmit impulse of a specific pulse duration, in particular a plurality of subsequent transmit pulses. The transducer elements can for example be arranged in a one-dimensional row, for example for providing a two-dimensional image that can be moved or swiveled around an axis mechanically. Further, the transducer elements may be arranged in a two-dimensional array, in particular for providing a multi-planar or three-dimensional image.

In general, the multitude of two-dimensional images, each along a specific acoustic line or scanning line, in particular scanning receive line, may be obtained in three different ways. First, the user might achieve the multitude of images via manual scanning. In this case, the ultrasound probe may comprise position-sensing devices that can keep track of a location and orientation of the scan lines or scan planes. However, this is currently not contemplated. Second, the transducer may be automatically mechanically scanned within the ultrasound probe. This may be the case if a one dimensional transducer array is used. Third, and preferably, a phased two-dimensional array of transducers is located within the ultrasound probe and the ultrasound beams are electronically scanned. The ultrasound probe may be handheld by the user of the system, for example medical staff or a doctor. The ultrasound probe 14 is applied to the body of the patient 12 so that an image of an anatomical site in the patient 12 is provided.

Further, the ultrasound system 10 has a controlling unit 16 that controls the provision of a three-dimensional image via the ultrasound system 10. As will be explained in further detail below, the controlling unit 16 controls not only the acquisition of data via the transducer array of the ultrasound probe 14 but also signal and image processing that form the three-dimensional images out of the echoes of the ultrasound beams received by the transducer array of the ultrasound probe 14.

The ultrasound system 10 further comprises a display 18 for displaying the three-dimensional images to the user. Further, an input device 20 is provided that may comprise keys or a keyboard 22 and further inputting devices, for example a track ball 24. The input device 20 might be connected to the display 18 or directly to the controlling unit 16.

Figure 2:
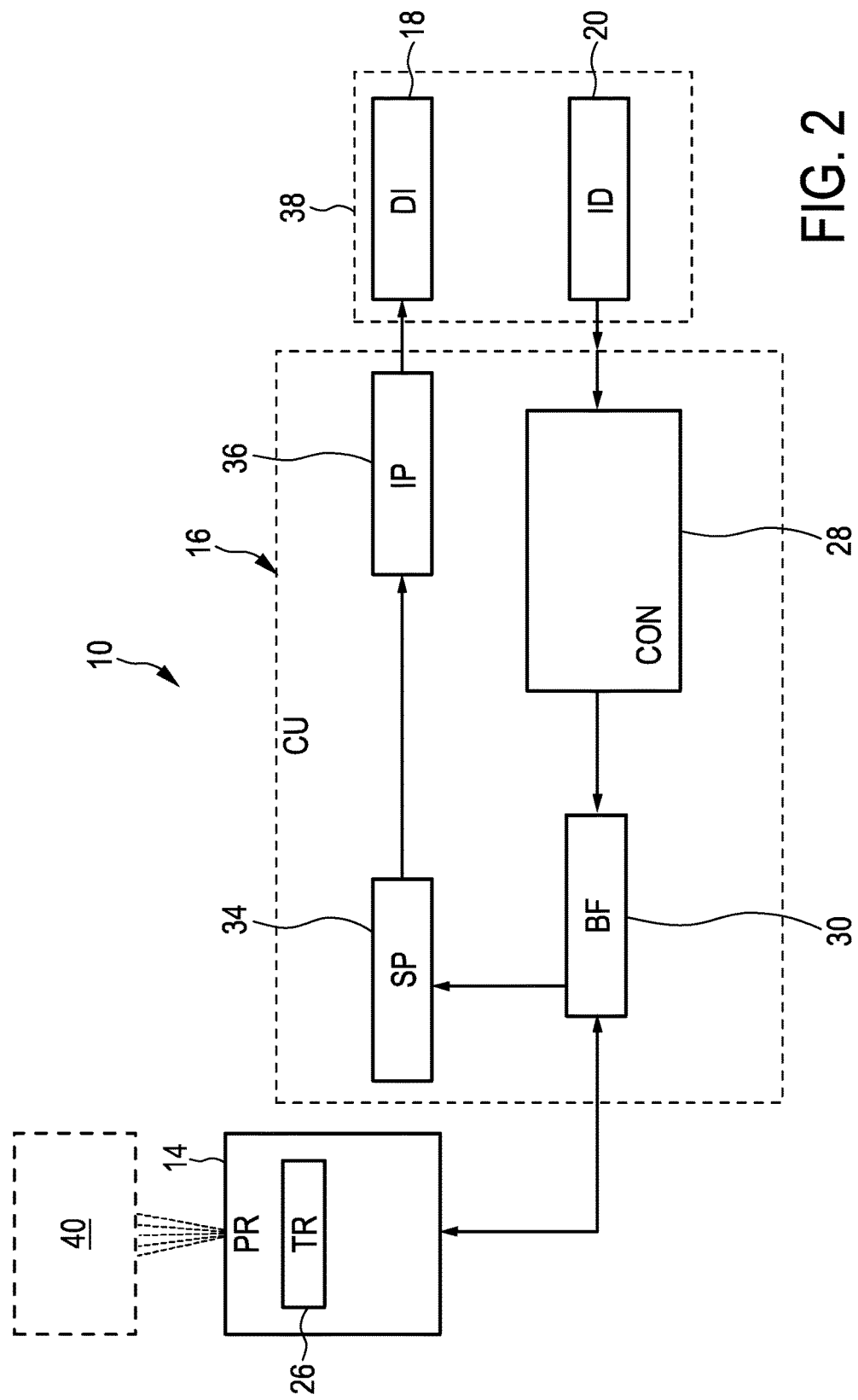
FIG. 2 shows a schematic block diagram of an ultrasound system according to a refinement of the ultrasound system in FIG. 1.

FIG. 2 shows a schematic block diagram of the ultrasound system 10. As already laid out above, the ultrasound system 10 comprises an ultrasound probe (PR) 14, the controlling unit (CU) 16, the display (DI) 18 and the input device (ID) 20. As further laid out above, the probe 14 comprises a phased two-dimensional transducer array 26. In general, the controlling unit (CU) 16 may comprise a central processing unit 28 that may include analog and/or digital electronic circuits, a processor, microprocessor or the like to coordinate the whole image acquisition and provision. However, it has to be understood that the central processing unit 28 does not need to be a separate entity or unit within the ultrasound system 10. It can be a part of the controlling unit 16 and generally be hardware or software implemented. The current distinction is made for illustrative purposes only.

The central processing unit 28 as part of the controlling unit 16 may control a beam former and, by this, what images of the volume 40 are taken and how these images are taken. The beam former 30 generates the voltages that drives the transducer array 26, determines parts repetition frequencies, it may scan, focus and apodize the transmitted beam and the reception or receive beam(s) and may further amplify filter and digitize the echo voltage stream returned by the transducer array 26. Further, the central processing unit 28 of the controlling unit 16 may determine general scanning strategies. Such general strategies may include a desired volume acquisition rate, lateral extent of the volume, an elevation extent of the volume, maximum and minimum line densities, scanning line times and the line density.

The beam former 30 further receives the ultrasound signals from the transducer array 26 and forwards them as image signals.

Further, the ultrasound system 10 comprises a signal processor 34 that receives the image signals. The signal processor 34 is generally provided for analogue-to-digital-converting, digital filtering, for example, band pass filtering, as well as the detection and compression, for example a dynamic range reduction, of the received ultrasound echoes or image signals. The signal processor forwards image data.

Further, the ultrasound system 10 comprises an image processor 36 that converts image data received from the signal processor 34 into display data finally shown on the display 18. In particular, the image processor 36 receives the image data, preprocesses the image data and may store it in an image memory. These image data is then further post-processed to provide images most convenient to the user via the display 18. In the current case, in particular, the image processor 36 may form the three-dimensional images out of a multitude of two-dimensional images acquired.

A user interface is generally depicted with reference numeral 38 and comprises the display 18 and the input device 20. It may also comprise further input devices, for example, a trackball, a mouse or further buttons which may even be provided on the ultrasound probe 14 itself. Further, the central processing unit 28 receives all data input by a user via the input device 20 and controls the output to the user via the display 18 and the image processor 36. Hence, the central processing unit 28 may also control the whole user interface 38.

A particular example for a three-dimensional ultrasound system which may apply the current invention is the CX50 CompactXtreme Ultrasound system sold by the applicant, in particular together with a X7-2t TEE transducer of the applicant or another transducer using the xMATRIX technology of the applicant. In general, matrix transducer systems as found on Philips iE33 systems or mechanical 3D/4D transducer technology as found, for example, on the Philips iU22 and HD15 systems may apply the current invention.

Figure 3:
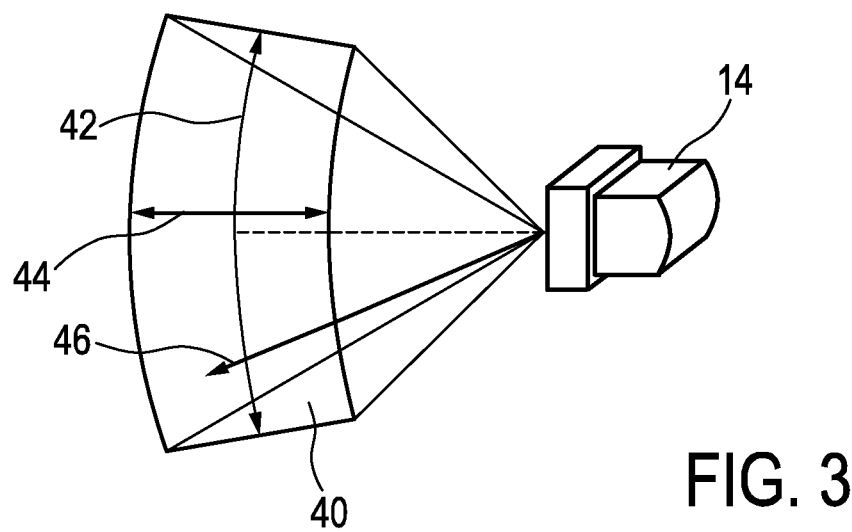
FIG. 3 shows a schematic representation of an exemplary volume in relation to an ultrasonic probe.

FIG. 3 shows an example of a volume 40 relative to the ultrasound probe 14. The exemplary volume 40 depicted in this example is of a sector type, due to the transducer array of the ultrasound probe 14 being arranged as a phased two-dimensional electronically scanned array. Hence, the size of the volume 40 may be expressed by an elevation angle 42 and a lateral angle 44. A depth 46 of the volume 40 may be expressed by a so-called line time in seconds per line. That is the scanning time spent to scan a specific scanning line. During image acquisition, the two-dimensional transducer array of the ultrasound probe 14 is operated by the beam former 30 in a way that the volume 40 is scanned along a multitude of scan lines sequentially. However, in multi-line receive processing, a single transmit beam might illuminate a multitude, for example four, receive scanning lines along which signals are acquired in parallel. If so, such sets of receive lines are then electronically scanned across the volume 40 sequentially.

FIGS. 4a and 4b show a schematic representation of screen shots of an image 50. The image 50 shows a structure 52 within the volume 40 that has been scanned. Further, it is shown how an in-plane measurement of a distance is conducted according to the prior art. The figures provide regular screen shots of three-dimensional images 50 of a volume 40 that may be provided on state of the art for ultrasound imaging systems.

In the three-dimensional image 50 a structure 52 is displayed as it was processed out of the data acquired by the transducer array 26 and processed via the signal processor 34 and the image processor 36. The structure 52, for example, may be any part of an anatomical side of a patient, for example such as a vessel, a heart or, as depicted in the following figures, different ripples in a corrugated curved surface.

In case a user would like to measure a distance when viewing the image 50 in FIG. 4a, the user might select a first point 54 and a second point 56. As is derivable from FIG. 4b, a distance 58 between the points 54 and 56 equals an actual distance between the two points on the structure 52 that the user had marked when viewing the image 50 in FIG. 4a. Hence, a linear measurement path 60 between the first point 54 and the second point 58 will result in the actual distance between the two points 54, 56 to be determined as the distance 58 shown to a user.

However, FIGS. 5a and 5b show the case in which the two points 54 and 56 do not lie within a same viewing plane as shown in the image 50 in FIG. 5a. If a user marks the two points 54 and 56 in the image 50 in FIG. 5a, the distance between the two points 54, 56 determined by the ultrasound imaging system 10 will be shorter than the actual distance between the two point 54, 56 on the structure 52. This means that has not marked points that the user would like have marked when viewing the image 50 in FIG. 5a.

This is clearly derivable from FIG. 5b. FIG. 5b shows the structure of FIG. 5a rotated by 90°. A plane 62 corresponds to the plane shown to the user when viewing the image 50 in FIG. 5a. As it is derivable from FIG. 5b, the first point 54 lies within the plane 62 as the corresponding part of the structure 52 also lies within the plane 62. However, as the structure 52 extends through the volume 40, a second point 56 the user has selected when viewing the image 50 in FIG. 5a, does not correspond to a true second point 64 on the structure 52 the user would like have selected when viewing the image 50 in FIG. 5a. Hence, as only a distance along the measurement path 60 and within the plane 62 is determined, the distance determined between the two points 54 and 56 will be shorter than the actual distance. However, it is the actual distance the user would like to be determined by the ultrasound imaging system 10. This is called the "foreshortening effect".

Figure 6A:
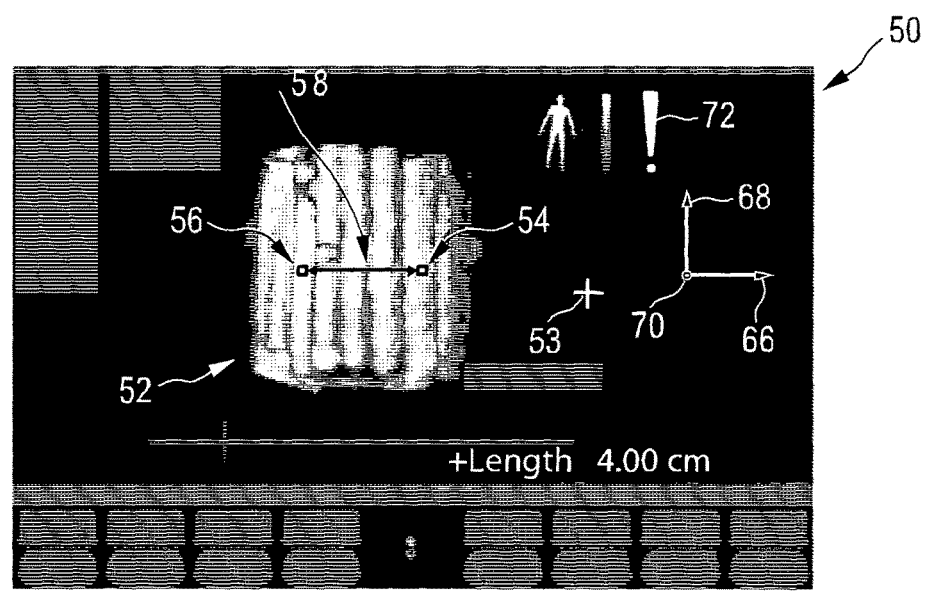
FIG. 6a and FIG. 6b show an in plane measurement of a distance between two points according to an embodiment.
Figure 6B:
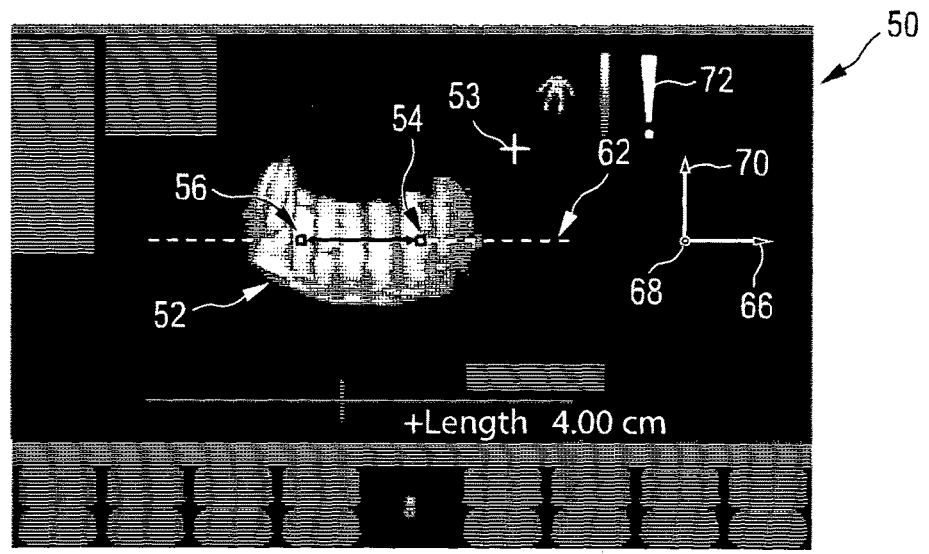

FIGS. 6a and 6b show an in-plane measurement of a distance 58 between the first point 54 and the second point 56 according to an embodiment. The user is shown an image 50 of the volume 40 as depicted in FIG. 6a. The image 50 is within the plane 62. Within the plane 62, a first coordinate 66 (e.g. the X-dimension) and a second coordinate 68 (e.g. the Y-dimension) of each of the points 54, 56 may be determined. For example, this may be conducted by moving a cursor 53 through the image and, hence, through the plane 62. The user may move the cursor 53 over the structure 52 and a point of the structure 52 that should form one of the endpoints of a distance 58 to be measured. Thus, the user would move the cursor in the plane 62 and the view as shown in FIG. 6a to, for example, the location of the first point 54. Then, the user may confirm the location of the cursor 53 by hitting a corresponding button or else. Now, without changing the view as shown in FIG. 6a, the user may be given an in-depth control to place the cursor 53 properly in the third dimension 70. As a movement of the cursor 53 in the third dimension 70 will not be recognizable for a user when viewing the image 50 as shown in FIG. 6a, a visual indicator 72 is provided on the display 18 and in the image 50 to inform the user that the cursor 53 has touched the structure 52. The exclamation mark shown as the visual indicator 72 in FIG. 6a is of merely exemplary nature. Other symbols or phrases may be used that may only be visible if the cursor actually touches the structure 52. Alternatively or additionally, it may be provided that the cursor 53, according to a hidden line mechanism, disappears when it enters the structure 52. Further, it may be provided that the cursor lights up and/or that the structure 52 lights up when the cursor and the structure 52 collide.

Moving the cursor 53 within the plane 62 is called a "first movement". Moving the cursor 53 perpendicularly to the plane 62 is called a "second movement". As the first movement and the second movement have been described as being conducted subsequently, it has to be emphasized that this is only one possible embodiment of conducting the first and second movements. It may also be provided that the first and second movements are conducted simultaneously.

Figure 7A:
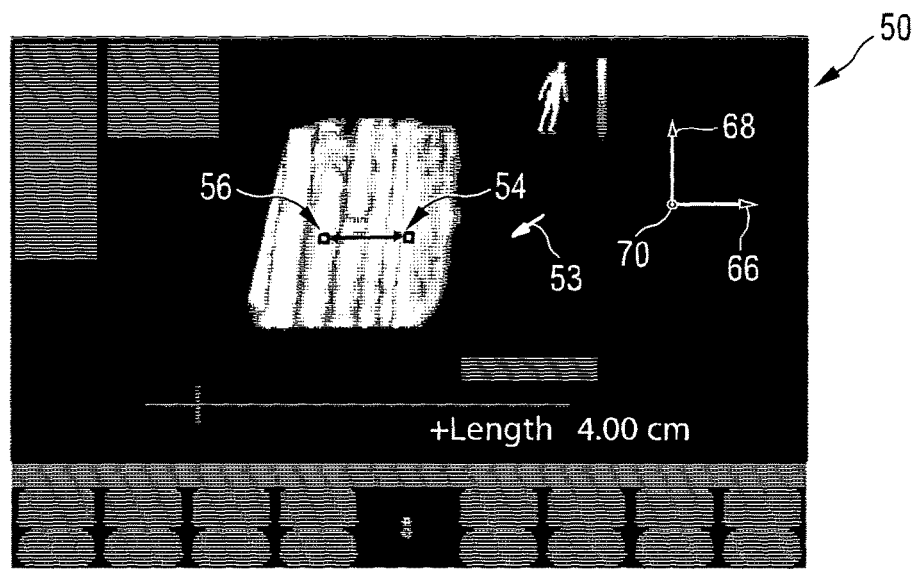
FIG. 7a and FIG. 7b show an out of plane measurement of a distance between two points according to an embodiment avoiding the "fore-shortening effect"
Figure 7B:
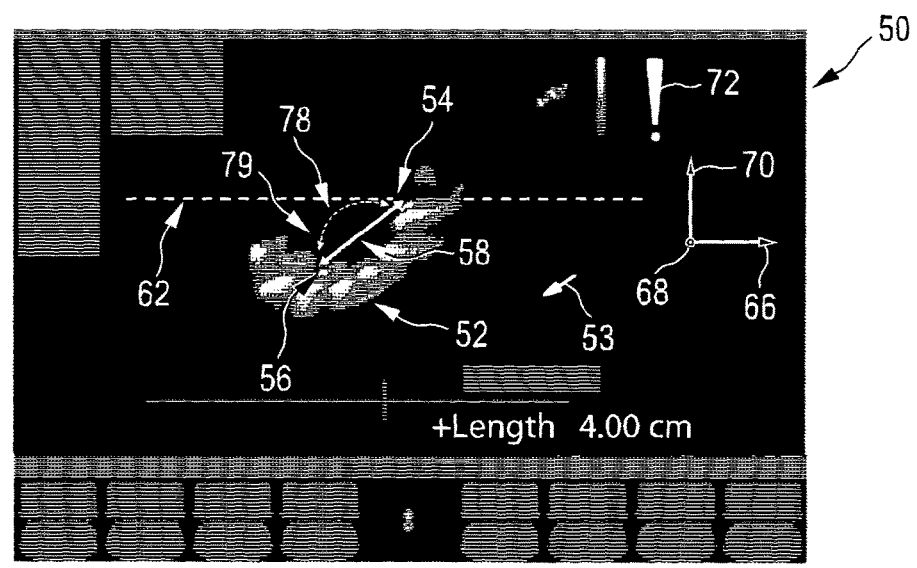

FIGS. 7a and 7b show how this "in-depth control" of the cursor 53 may avoid the fore-shortening effect.

First, as shown in FIGS. 7a and 7b, the cursor 53 may be of any form suitable. It may have the form of an arrow, a cross hair or else to properly identify the parts of the structure 52 that the user may want to select.

As explained above, the user may now select in the view as shown in FIG. 7a the first point 54 by first moving the cursor 53 in the plane 62 to determine the first and second coordinates 66, 68 and then perform a second movement of the cursor 53 in the third dimension 70 into the depth of the volume 40 until the cursor 53 and the structure 52 collide as indicated by the visual indicator 72. The second point 56 may then be selected the same way.

As it is derivable from a view rotated by 90° and shown in FIG. 7b, by this, a distance 58 between the two points 54, 56—wherein the second point 56 is not lying within the plane 62 can be properly determined. The first point 54 and the second point 56 can be set touching the structure 52. Further, this all can be done without changing the view as depicted in FIG. 7a. Then, the distance 58 between the first point 54 and the second point 56 can be properly determined.

Additionally or alternatively to the visual indicator 72, also an audio indicator or a tactually sensible indicator may be provided. Referring back to FIG. 1, the display 18 or any other part of the ultrasound imaging system 10 may comprise a speaker 73 that may be configured to make a noise or tone in case the cursor 53 collides with the structure 52 to provide an audio indicator 74.

Further, again additionally or alternatively to the visual and audio indicators 72, 74, a tactually sensible indicator 76 may be provided, for example by including a rumble mechanism 75 into the input device 20. By this, the user may feel when the cursor collides with the volume when using the input device 20 to move the cursor to 53 around the volume.

Further, the ultrasound imaging system 10 may be configured so as to provide the user with a possibility to measure the distance between the first point 54 and the second point 56 not only as the shortest distance along a straight line connecting both points 54, 56, but also along any other measurement path 78. To define this alternative measurement path 78, the user may set up further points 79 in the volume by conducting the first movement and the second movement as explained above or may apply standard geometrical forms, for example an ellipse, to connect the first point 54 and the second point 56.

Figure 8:
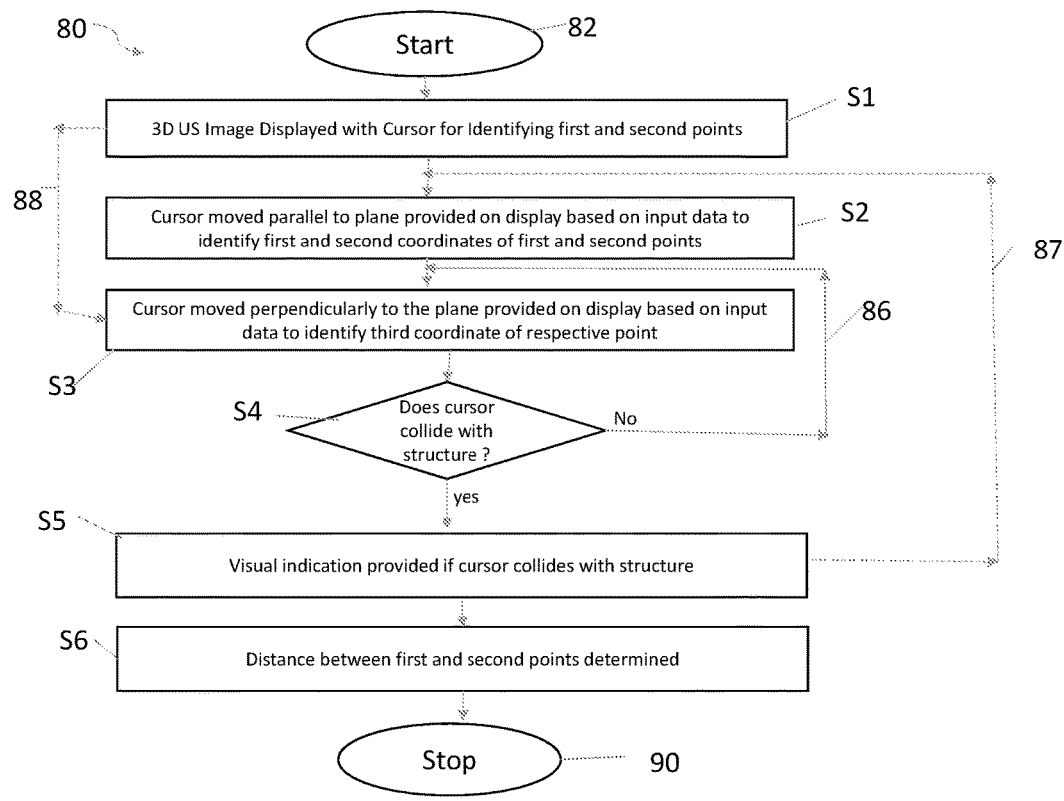
FIG. 8 shows a schematic flow diagram of a method according to an embodiment.

FIG. 8 shows a schematic block diagram of an embodiment of a method 80. The method starts at a step 82. In the first step S1, a three-dimensional ultrasound image 50 is shown on a display 18 together with the cursor 53 for identifying the first point 54 and the second point 56. Such an image may be one of the images as shown in FIGS. 6a and 7a.

Then, in step S2, the cursor is moved parallel to a plane provided on the display 18 based on input data by a user to identify a first coordinate 66 and a second coordinate 68 of at least one of the first and second points 54, 56.

After the first coordinates 66 and the second coordinate 68 have been defined, in a step S3, the cursor 53 is moved perpendicularly to the plane 62 provided on the display based on input data by the user to identify a third coordinate 70 of the respective point.

When this second movement in step S3 is conducted, in a step S4, it is controlled whether the cursor 53 collides with the structure 52. If not, no amendments to the display do occur and the method runs in a loop as indicated by line 86. If so, an indication is given that the cursor 53 collides with the structure 52. This may a visual indication 72, an audio indication 74 or a tactual indication 76 as explained above. The respective indication is given in a step S5. Now, the third coordinate 70 may be set. In case only one point has been defined so far, the method returns back before step S2 is indicated by arrow 87 to also define the coordinates of the respective second point.

After both points have been defined, in a step S6, the distance 58 between the two points 54 and 56 is determined. The method then ends in a step 90.

However, the steps S2 and S3 do not necessarily have to be conducted subsequently. It may also be possible that the first movement within the plane and the second movement perpendicularly to the plane may be conducted in parallel directly after step S1 as indicated by arrow 88 in dashed lines. The user may then simultaneously move the cursor 53 to define all three coordinates 66, 68, 70 at the same time.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system for providing a three-dimensional image of a volume within anatomy of a patient, the ultrasound imaging system comprising:
   a transducer array configured to be placed adjacent to the anatomy and provide an ultrasound receive signal;
   one or more processors configured to receive the ultrasound receive signal and to provide display data representing the three-dimensional image of the volume, wherein the three-dimensional image of the volume comprises a structure;
   a display configured to receive the display data and to provide the three-dimensional image of the volume, wherein the display is further configured to provide a cursor movable within the three-dimensional image of the volume; and
   an input device configured to provide input data to the one or more processors, wherein the input data includes a movement of the cursor,
   wherein the one or more processors are further configured to determine a distance, without foreshortening, between a first point on the structure and a second point on the structure, wherein the one or more processors determining the distance includes:
   causing a first movement of the cursor in a X-Y plane of the three-dimensional image;
   receiving a selection of the first point on the structure based on the first movement of the cursor, wherein the first point is located in the X-Y plane;
   causing a second movement of the cursor in a X-Z plane of the three-dimensional image while the structure remains in a same orientation in the three-dimensional image as during the first movement of the cursor, wherein the X-Z plane is normal to the X-Y plane;
   causing a display of a visual representation of a collision between the cursor and a surface of the structure during the second movement of the cursor in the X-Z plane;
   receiving a selection of the second point based on the visual representation of the collision such that the second point is on the structure and not in space around the structure in the three-dimensional image, wherein the second point is located in the X-Z plane; and
   determining the distance between the first point and the second point.

2. The system of claim 1, wherein the one or more processors are configured to cause the second movement after the first movement has been completed.

3. The system of claim 1, wherein the one or more processors are configured to cause the second movement and the first movement simultaneously.

4. The system of claim 1, wherein the visual representation of the collision is displayed on the display.

5. The system of claim 4, wherein the visual representation of the collision is a change in an appearance of the cursor or a tag showing up on the display.

6. The system of claim 5, wherein the change in the appearance of the cursor causes the cursor to light-up or to disappear.

7. The system of claim 1, wherein the visual representation of the collision is a change of an appearance of the structure within the volume.

8. The system of claim 1, wherein the ultrasound imaging system further comprises a speaker, and wherein the representation of the collision further comprises an audio indication provided via the speaker.

9. The system of claim 1, wherein the representation of the collision further comprises a tactually sensible indication provided via the input device.

10. The system of claim 1, wherein the one or more processors are configured to enable inputting a measurement path between a first point and a second point identified in the three-dimensional image of the volume, and wherein the distance between the first point and the second point is determined along the measurement path.

11. The system of claim 10, wherein the one or more processors are configured to input the measurement path by identifying at least one further point within the volume and selecting a geometric form to connect the first point and the second point.

12. The system according to claim 1, further comprising:
   a beam former configured to control the transducer array to scan the volume along a multitude of scanning lines, and further configured to receive the ultrasound receive signal and to provide an image signal, wherein the one or more processors comprise:
   a signal processor configured to receive the image signal and to provide image data; and
   an image processor configured to receive the image data from the signal processor and to provide display data.

13. The system according to claim 1, wherein the structure is an anatomical feature.

14. The system according to claim 13, wherein the structure includes a portion of a vessel.

15. The system according to claim 13, wherein the structure includes a portion of a heart.

* * * * *